US012116444B2

(12) United States Patent
Conradi et al.

(10) Patent No.: US 12,116,444 B2
(45) Date of Patent: Oct. 15, 2024

(54) POLYMERIC ANION-CONDUCTING MEMBRANE

(71) Applicant: Evonik Operations GmbH, Essen (DE)

(72) Inventors: Oliver Conradi, Düsseldorf (DE); Artjom Maljusch, Bochum (DE); Harald Rögl, Wallern an der Trattnach (AT)

(73) Assignee: Evonik Operations GmbH, Essen (DE)

( * ) Notice: Subject to any disclaimer, the term of this patent is extended or adjusted under 35 U.S.C. 154(b) by 1159 days.

(21) Appl. No.: 16/651,467

(22) PCT Filed: Oct. 16, 2018

(86) PCT No.: PCT/EP2018/078184
§ 371 (c)(1),
(2) Date: Mar. 27, 2020

(87) PCT Pub. No.: WO2019/076860
PCT Pub. Date: Apr. 25, 2019

(65) Prior Publication Data
US 2020/0262959 A1    Aug. 20, 2020

(30) Foreign Application Priority Data

Oct. 17, 2017   (EP) ..................................... 17196802

(51) Int. Cl.
| | | |
|---|---|---|
| B01J 41/13 | (2017.01) | |
| C07D 235/18 | (2006.01) | |
| C08F 295/00 | (2006.01) | |
| C08G 65/40 | (2006.01) | |
| C25B 13/08 | (2006.01) | |

(52) U.S. Cl.
CPC ............. *C08F 295/00* (2013.01); *B01J 41/13* (2017.01); *C07D 235/18* (2013.01); *C08G 65/4006* (2013.01); *C08G 65/4037* (2013.01); *C25B 13/08* (2013.01)

(58) Field of Classification Search
CPC ...... C08F 295/00; B01J 41/13; C07D 235/18; C08G 65/4006; C08G 65/4037; C25B 13/08
See application file for complete search history.

(56) References Cited

U.S. PATENT DOCUMENTS

| | | | |
|---|---|---|---|
| 3,817,749 A | 6/1974 | Kitahara et al. | |
| 7,632,591 B2 | 12/2009 | Won et al. | |
| 7,687,668 B2 | 3/2010 | Rogl et al. | |
| 7,812,099 B2 | 10/2010 | Roegl et al. | |
| 2004/0121210 A1 | 6/2004 | Hamrock et al. | |
| 2007/0100131 A1* | 5/2007 | Hung ................. | C08G 65/4056 528/373 |
| 2009/0325030 A1 | 12/2009 | Hamrock et al. | |
| 2014/0014519 A1 | 1/2014 | Ohmura et al. | |
| 2016/0032072 A1 | 2/2016 | Rhine et al. | |
| 2019/0016851 A1* | 1/2019 | Holdcroft ............... | C25B 13/08 |

FOREIGN PATENT DOCUMENTS

| | | |
|---|---|---|
| EP | 0126231 B1 | 12/1989 |
| EP | 2296210 A1 | 3/2011 |
| EP | 2606954 A1 | 6/2013 |
| EP | 2224523 B1 | 7/2014 |
| TW | 200718727 A1 | 5/2007 |
| WO | 2005/045978 A2 | 5/2005 |
| WO | 2013/149328 A1 | 10/2013 |
| WO | WO-2017117678 A1 * | 7/2017 ......... B01D 67/0009 |

OTHER PUBLICATIONS

German language International Search Report mailed on Dec. 19, 2018 in PCT/EP2018/078184 (3 pages).
German language Written Opinion mailed on Dec. 19, 2018 in PCT/EP2018/078184 (4 pages).
Hying et al., U.S. Appl. No. 16/702,752, filed Dec. 4, 2019.
International Search Report mailed on Dec. 19, 2018 in PCT/EP2018/078184 (2 pages).
Conradi et al., U.S. Appl. No. 17/629,285, filed Jan. 21, 2022.
Wright et al., "Poly(phenylene) and m-Terphenyl as Powerful Protecting Groups for the Preparation of Stable Organic Hydroxides," copyright 2016, Angewandte Chemie International Edition, 55(15), pp. 4818-4821 (4 pages).
Weissbach et al., "Simultaneous, Synergistic Control of Ion Exchange Capacity and Crosslinking of Sterically-Protected Poly(benzimidazolium)s," copyright 2016, Chemistry of Materials, pp. 8060-8070 (11 pages).
European Search Report mailed on Apr. 19, 2018 in EP 19176802.7 (5 pages).

* cited by examiner

*Primary Examiner* — Michael M Dollinger
*Assistant Examiner* — Christina H. W. Rosebach
(74) *Attorney, Agent, or Firm* — Michael Best & Friedrich LLP

(57) ABSTRACT

The present invention provides compounds, especially polymeric compounds, having at least one imidazole and/or imidazolium structural unit, a process for preparation thereof and for the use thereof.

17 Claims, No Drawings

POLYMERIC ANION-CONDUCTING MEMBRANE

CROSS REFERENCE TO RELATED APPLICATIONS

This application is a 35 U.S.C. § 371 U.S. national phase entry of International Application No. PCT/EP2018/078184 having an international filing date of Oct. 16, 2018, which claims the benefit of European Application No. 17196802.7 filed Oct. 17, 2017, each of which is incorporated herein by reference in its entirety.

FIELD

The present invention provides compounds, especially polymeric compounds, having at least one imidazole and/or imidazolium structural unit, a process for preparation thereof and for the use thereof, especially as anion-conducting membranes.

BACKGROUND

Polymeric ion-conducting membranes have long been known. The membranes described in WO 2005/045978 A2, US 2009325030 A1 and US 20040121210 A1 are based on a highly fluorinated polymer backbone.

In EP 2224523 B1 and US 20140014519 A1, anion-conducting membranes are produced, in which a porous film is impregnated with a mixture of various monomers having vinyl groups, at least one of which has a halogen group (chlorine group), the surfaces of the porous film are each covered with a polyester film and then a thermal polymerization is conducted. The material thus obtained is then treated with trimethylamine or methyl iodide and then with NaOH. In EP 2296210 A1, the treatment with trimethylamine is followed by a treatment with $Na_2CO_3$.

In EP 2606954 A1, anion-conducting membranes are obtained by the curing of a polymer solution containing polymers that have been obtained by chloromethylation of polysulfones and subsequent treatment with trimethylamine.

The prior art also discloses various polymers in which molecules and/or molecular units corresponding to the following formulae (Ia) and (Ib) are present:

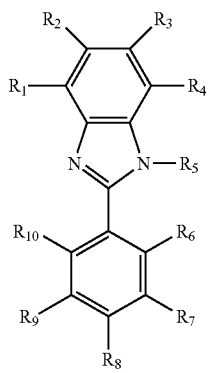

(Ia)

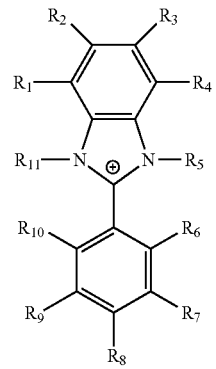

(Ib)

WO 2013/149328 describes polymers in which units of the formula (Ib) are present, in which
$R_1$, $R_2$, $R_3$ and $R_4$ are the same or different and are —H, any desired group or a polymer radical,
$R_5$ and $R_{11}$ are the same or different and are methyl, trifluoromethyl, alkyl, perfluoroalkyl, heteroalkyl, aryl, aralkyl or a polymer radical or no group,
$R_6$ and $R_{10}$ are the same or different and are methyl, trifluoromethyl, alkyl, perfluoroalkyl, heteroalkyl, alkoxy, perfluoroalkoxy, halogen, aryl, heteroaryl or a polymer radical, and
$R_7$, $R_8$ and $R_9$ are the same or different and are —H, any desired group or a polymer radical.

Particular embodiments described are those polymers in which the unit (Ib) is incorporated into the polymer via the $R_3$ and $R_5$ radicals, via the $R_5$ radical, via the $R_5$ radical or via the $R_5$ and $R_{11}$ radicals. In the examples, the units (Ia) and (Ib) described are 2-phenylbenzimidazole, 2-mesitylbenzimidazole, 1,3-dimethyl-2-mesitylbenzimidazolium, 1,3-dimethyl-2-phenylbenzimidazolium, poly(2,2'-(m-phenyl)-5,5'-dibenzimidazole), poly(2,2'-(m-phenyl)-5,5'-bis (N,N'-dimethylbenzimidazolium) iodide), poly(2,2'-(m-mesityl)-5,5'-dibenzimidazole) and poly(2,2'-(m-mesityl)-5,5'-bis(N,N'-dimethylbenzimidazolium) iodide).

EP 0126231 B1 describes molecules or polymers in which units of the formula (Ia) or (Ib) are present, in which
$R_1$, $R_2$, $R_3$ and $R_4$=—H,
$R_5$ and $R_{11}$ are the same or different and are H—, a hydrocarbyl radical having 1 to 10 carbon atoms or carboxyalkyl radical having 2 to 10 carbon atoms, preferably methyl, ethyl, benzyl or carboxymethyl radical,
$R_8$=vinyl radical or a polymer radical, and
$R_6$, $R_7$, $R_9$ and $R_{10}$ are the same or different and are —H or a hydrocarbyl group having 1 to 4 carbon atoms, preferably —H, methyl or ethyl radical.

U.S. Pat. No. 3,817,749 describes molecules of formula (Ia) with $R_1$, $R_2$, $R_3$, $R_4$, $R_5$, $R_7$, $R_8$ and $R_9$=—H and $R_6$ and $R_{10}$=Cl or Br. The molecules that have been reacted with acetylene and then polymerized are used as photosensitive polymers.

WO 2017/117678 and the corresponding publications by Steven Holdcroft describe polymers and the use thereof in ion-conducting membranes having units of the formula (Ib) with R10 and R6=phenyl radicals. Polymers described include poly(4,4"[2'-(1-methyl-1H-benzimidazol-2-yl)-m-terphenylene]) and poly(4,4"-[2'-(1,3-dimethyl-1H-benzimidazolium-2-yl)-m-terphenylene]) iodide.

SUMMARY

The problem addressed by the present invention was that of providing alternative compounds suitable as or for production of anion-conducting polymers.

It has been found that, surprisingly, this problem is solved by the compounds according to the claims.

The present invention therefore provides compounds as claimed in the claims and described hereinafter.

The present invention likewise provides a process for preparing such compounds and for the use thereof as anion-conducting membranes, and also these membranes themselves.

The polymers according to the invention have the advantage that they can be prepared in a simple manner.

The membranes produced therefrom have the advantage that these have high mechanical stability and low swelling characteristics combined with high dimensional stability. In addition, the membranes exhibit quite high anion conductivities.

The compounds, processes and uses according to the invention are described by way of example hereinafter, without any intention that the invention be restricted to these illustrative embodiments. When ranges, general formulae or classes of compounds are specified below, these are intended to encompass not only the corresponding ranges or groups of compounds which are explicitly mentioned but also all subranges and subgroups of compounds which can be obtained by leaving out individual values (ranges) or compounds. Where documents are cited in the context of the present description, their content shall fully form part of the disclosure content of the present invention, particularly in respect of the matters referred to. Percentages specified hereinbelow are by weight unless otherwise stated. Where average values are reported hereinafter, these are the numerical average, unless stated otherwise. Where properties of a material are referred to hereinafter, for example viscosities or the like, these are the properties of the material at 25° C., unless stated otherwise. Where chemical (empirical) formulae are used in the present invention, the specified indices may be not only absolute numbers but also average values.

DETAILED DESCRIPTION

The present invention provides compounds, preferably oligomers or polymers, more preferably polymers, containing at least one unit of the formula (Ia) or (Ib)

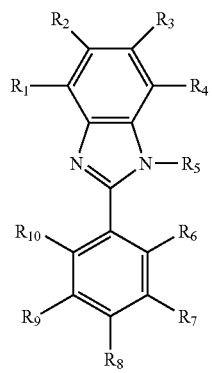

(Ia)

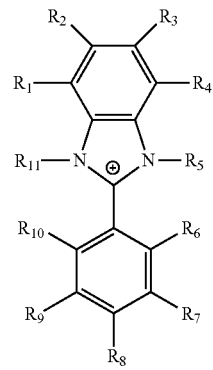

(Ib)

which are characterized in that $R_1$, $R_2$, $R_3$ and $R_4$ are the same or different and are —H or any desired group, preferably —H, $R_5$ and $R_{11}$ are the same or different and are alkyl or perfluoroalkyl, preferably a methyl, ethyl, propyl, isopropyl, n-butyl, tert-butyl or trifluoromethyl radical, more preferably a methyl radical, $R_6$ and $R_{10}$ are the same or different and are an oligomer or polymer radical; $R_6$ and $R_{10}$ are preferably a polymer radical, and $R_7$, $R_8$ and $R_9$ are the same or different and are —H or any desired group, preferably —H.

Particularly preferred polymers have at least one unit of the formula (Ia) or (Ib) as defined above, where at least one of the $R_6$ and $R_{10}$ radicals is an oligomer or polymer radical attached via an oxygen atom to the ring carbon atom ($R_6$ or $R_{10}$=—$OR_{16}$ with $R_{10}$=oligomer or polymer radical, preferably a polymer radical).

Preferably, the compounds of the invention are oligomers or polymers having at least 2 units of the formula (Ia) or (Ib), preferably (Ia). Particularly preferred compounds according to the invention are block copolymers.

The compounds according to the invention are preferably polymer compounds wherein the polymer radicals $R_6$ and $R_{10}$ have one or more units of the formula (IIa) and/or (IIb) and/or (IIIa) and/or (IIIb) and/or (IIIc) and/or (IIId)

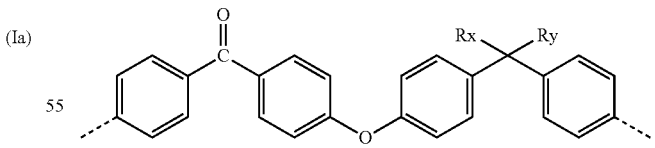

(IIa)

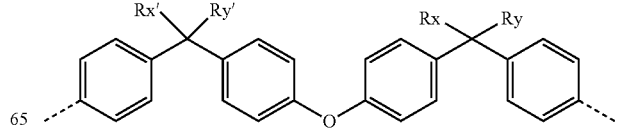

(IIb)

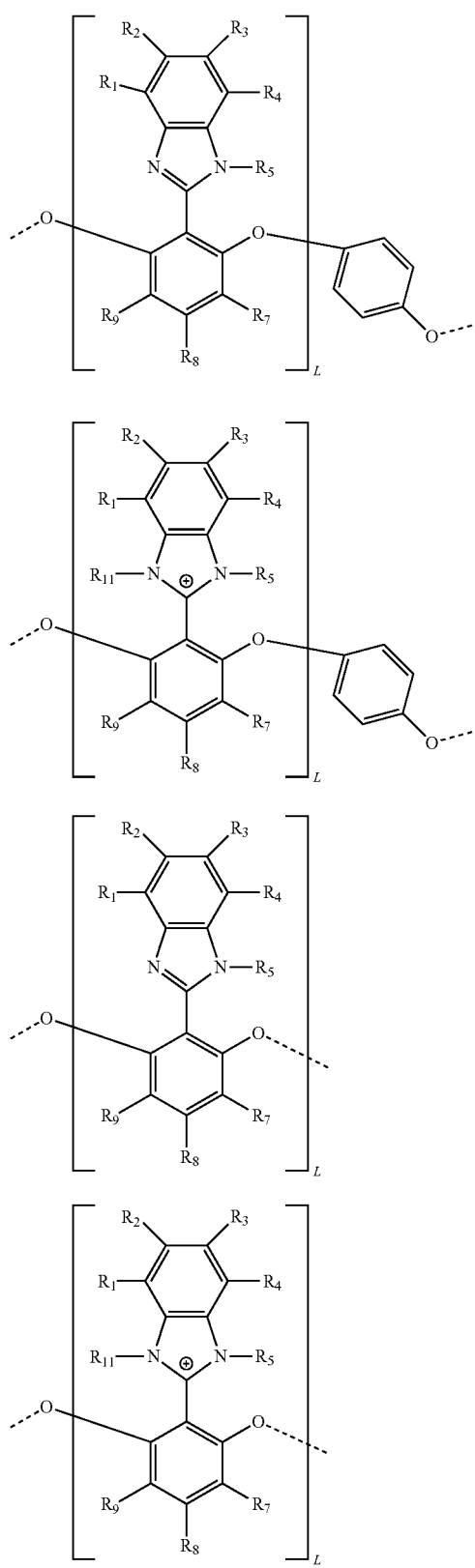
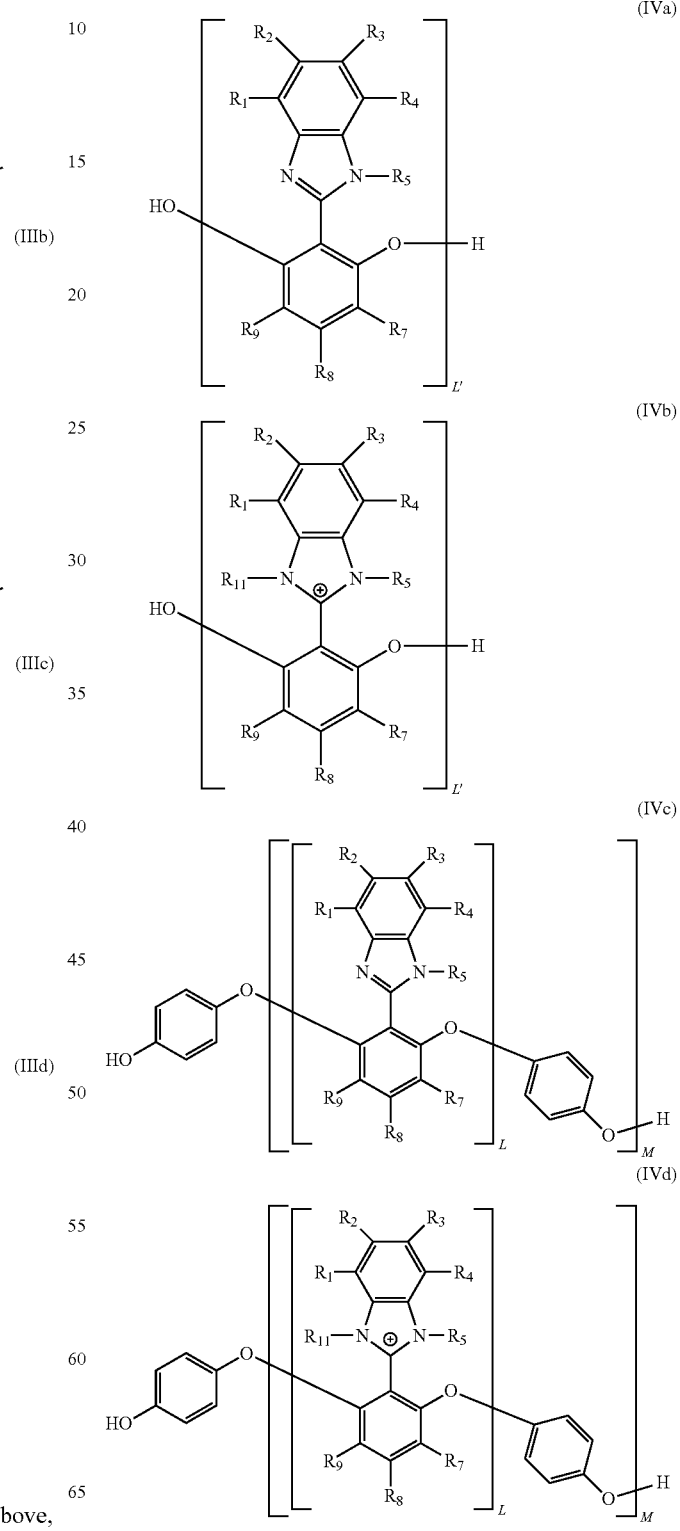
with $R_1$, $R_2$, $R_3$, $R_4$, $R_5$, $R_7$, $R_8$, $R_9$ and $R_{11}$ as defined above, L=1 to 25, preferably 1 to 15, more preferably 1 to 9, and where Rx and Ry and Rx' and Ry' are the same or different and are an alkyl, phenyl or perfluoroalkyl radical, preferably —$CH_3$ or —$CF_3$.
Preferred compounds according to the invention are compounds of the formula (IVa), (IVb), (IVc), (IVd), (IVe) and (IVf)

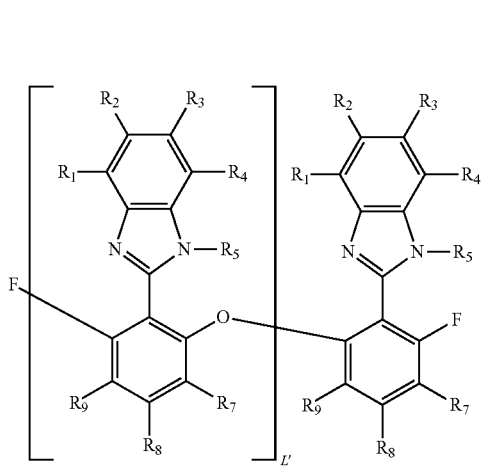

(IVe)

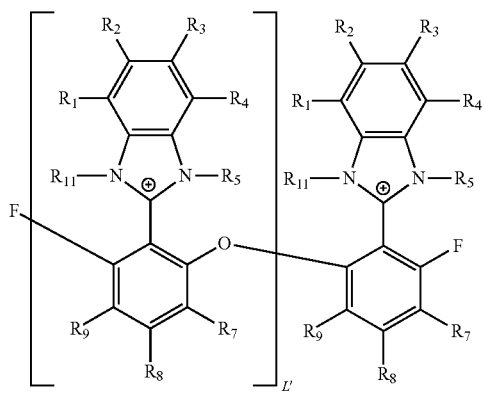

(IVf)

with $R_1$, $R_2$, $R_3$, $R_4$, $R_5$, $R_7$, $R_8$ and $R_9$ as defined above, L=1 to 25, preferably 1 to 15, more preferably 1 to 9, and L'=2 to 25, preferably 2 to 15, more preferably 3 to 9, and M=1 to 500.

Particularly preferred compounds according to the invention are compounds of the formula (Va) and (Vb)

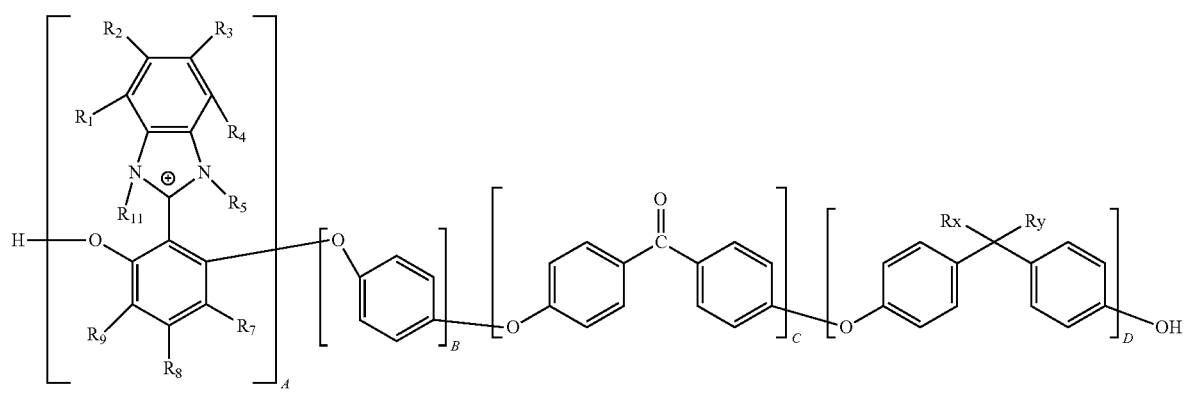

(Va)

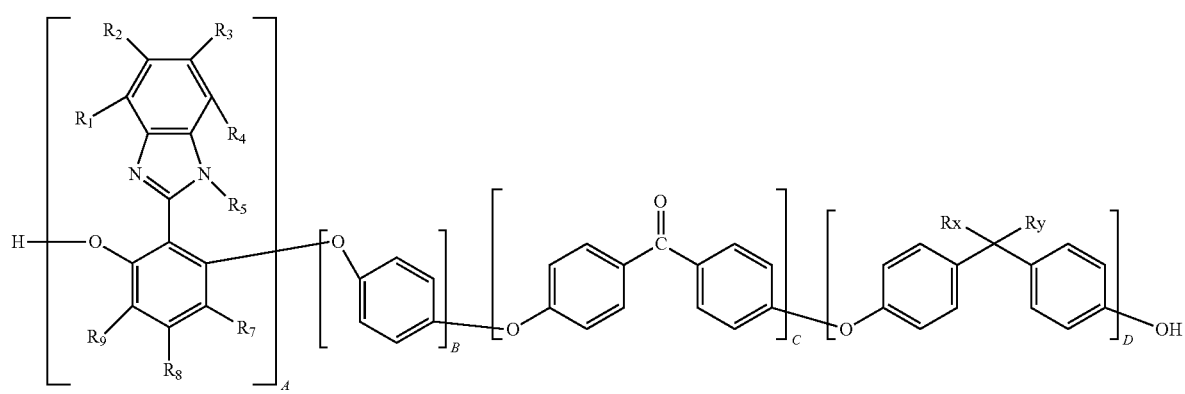

(Vb)

with $R_1$, $R_2$, $R_3$, $R_4$, $R_5$, $R_7$, $R_8$, $R_9$ and $R_{11}$ as defined above and where Rx and Ry are the same or different and are —$CH_3$ or —$CF_3$ and A=5 to 500, B=5 to 500, C=1 to 500 and D=0 to 1000, where the units indicated by the indices A, B, C and D may occur in blockwise or random distribution in the compound.

Very particularly preferred compounds are compounds of the formula (VIa) to (VId)
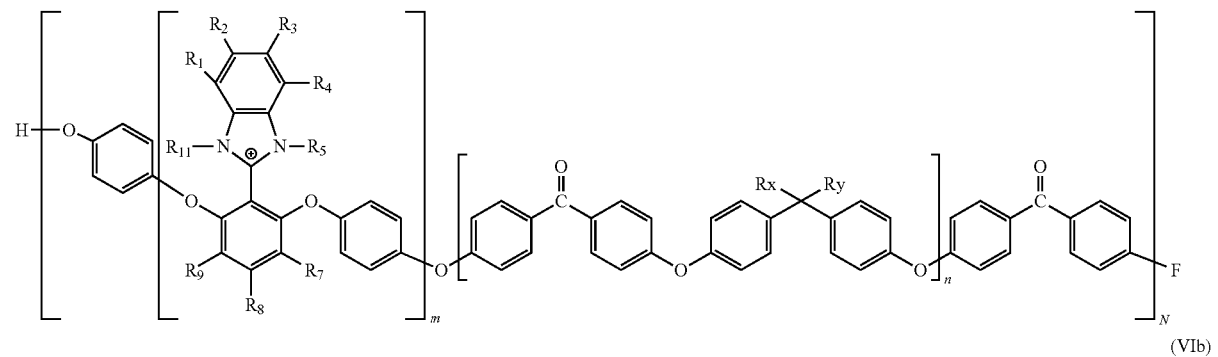
(VIa)
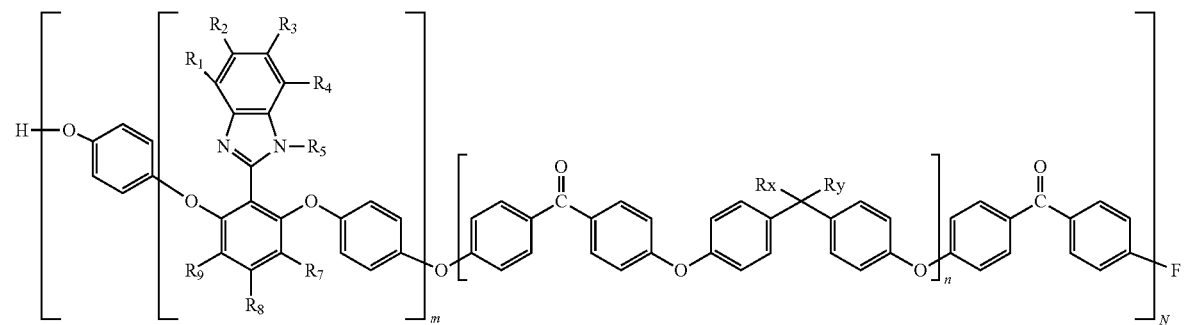
(VIb)
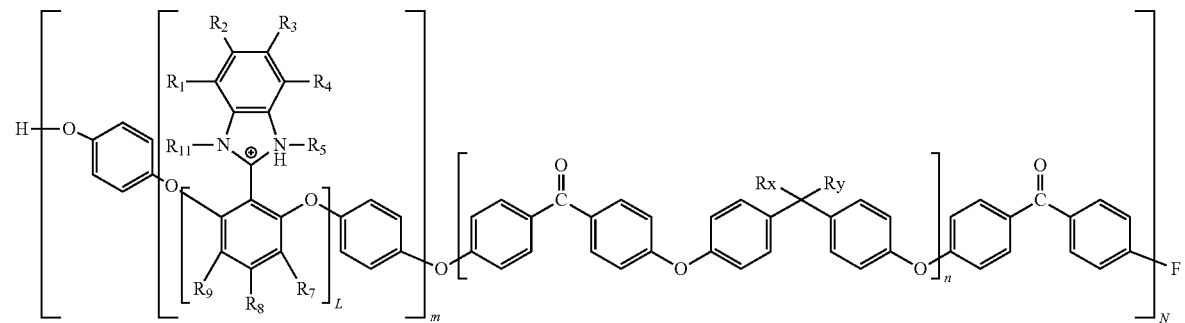
(VIc)
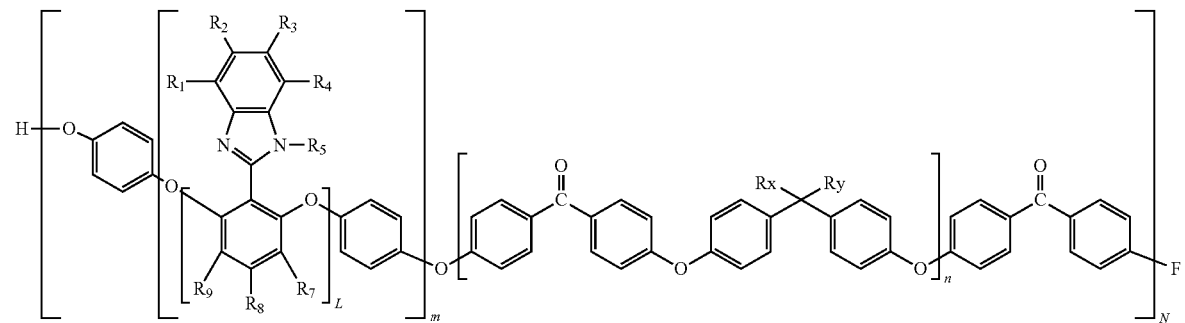
(VId)

with $R_1$, $R_2$, $R_3$, $R_4$, $R_5$, $R_7$, $R_8$, $R_9$ and $R_{11}$ as defined above, L=1 to 25, preferably 3 to 15, more preferably 3 to 9, and where Rx and Ry are the same or different and are —$CH_3$ or —$CF_3$ and m=1 to 500, n=1 to 500, preferably 5 to 50, and N=1 to 500, where the units indicated by the indices m, n and N may occur in blockwise or random distribution in the compound.

The compounds according to the invention can be obtained, for example, by the process described hereinafter.

It is a feature of the process according to the invention for preparation of the above-described compounds according to the invention that it includes a step (1) in which a compound of the formula (X)

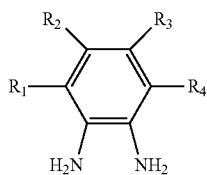

(X)

with $R_1$ to $R_4$ as defined above is reacted with a compound of the formula (XI)

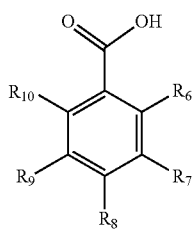

(XI)

with $R_6$ to $R_{10}$ as defined above, with the proviso that $R_6$ and $R_{10}$=—F, to give a compound (XII)

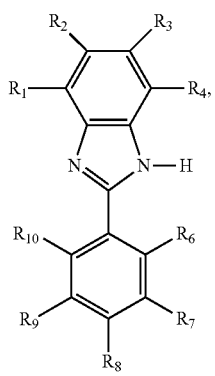

(XII)

and the compound of the formula (XII) is reacted with a methylating reagent or trifluoromethylating reagent to obtain a compound of the formula (Ia) as defined above where $R_5$=alkyl or perfluoroalkyl radical, preferably methyl, ethyl, propyl, isopropyl, n-butyl, tert-butyl or trifluoromethyl radical, more preferably methyl radical, and $R_6$ and $R_{10}$=—F.

Preferably, step (1) is conducted by initially charging polyphosphoric acid and methanesulfonic acid in a heatable reaction vessel at a temperature of 40 to 80° C., preferably of 55 to 65° C., and adding the compound of the formula (X) to this mixture while stirring and preferably while heating the reaction mixture to 90 to 130° C., preferably 105 to 115° C. Once this mixture has preferably been homogenized, the compound of the formula (XI) is added, preferably likewise while stirring. An organic solvent, preferably o-xylene, is preferably added to this reaction mixture, and the temperature of the reaction mixture is increased to 140 to 170° C., preferably to 150 to 160° C., within 3 hours and then left at this temperature for preferably 30 to 60 hours, more preferably 35 to 45 hours. This is followed by cooling, preferably to 65 to 95° C., preferably 75 to 85° C. On attainment of this temperature, water is preferably added. The addition is preferably effected in such a way that the temperature remains within the temperature range specified. After addition of the complete amount of water, which is preferably 100% to 500% by volume of the reaction mixture present in the reactor, the reactor contents are preferably cooled to 10 to 30° C., preferably 15 to 25° C. and more preferably 20° C. After stirring for preferably 1 to 5 hours, more preferably 1.5 to 2.5 hours, the reaction mixture obtained is preferably subjected to a separation process in which solids are separated from liquids. The solids removed are preferably stirred with water and, while cooling, such that the temperature is preferably from 30 to 60° C., preferably 40 to 50° C., an alkali, preferably NaOH, is added until the reaction mixture has attained a pH of preferably 10. After further stirring, the solids are separated again from the mixture, washed with water and dried. A compound of the formula (XII) is obtained.

To obtain a compound of the formula (Ia) with $R_6$ and $R_{10}$=—F and where $R_5$ is the same or different and is alkyl or perfluoroalkyl, preferably a methyl, ethyl, propyl, isopropyl, n-butyl, tert-butyl or trifluoromethyl radical, preferably methyl or trifluoromethyl radical, more preferably methyl radical, the compound of the formula (XII) can be contacted, for example in a reaction vessel, with an alkylating reagent, preferably dimethyl carbonate, $K_2CO_3$ and DMAc, and then reacted by heating to a temperature of 90 to 130° C., preferably while stirring. Preferably, the reaction is conducted over a period of 10 to 25 hours, preferably of 15 to 20 hours. It may be advantageous to end the reaction by adding water to the reaction mixture and, after the addition of water, preferably continuing to stir for 0.5 to 2 hours. A compound of the formula (Ia) with $R_5$=methyl is obtained.

The process according to the invention preferably has a process step (2) in which a compound of the formula (Ia) as defined above with $R_6$ and $R_{10}$=—F and $R_5$=alkyl or perfluoroalkyl, preferably a methyl, ethyl, propyl, isopropyl, n-butyl, tert-butyl or trifluoromethyl radical, is reacted with a silane, preferably $(CH_3)_3SiO^-K^+$, and then hydrolysed with KOH or NaOH to obtain a compound of the formula (Ia) with $R_{10}$ or $R_6$=—OH, referred to hereinafter as compound of the formula (Ia').

It may be advantageous when the process according to the invention has a process step (3) in which a compound of the formula (Ia) with $R_1$ to $R_5$ and $R_7$ to $R_9$ as defined above, and $R_6$ and $R_{10}$=fluorine, is reacted with at least one compound of the formula (Ia') with $R_1$ to $R_5$ and $R_7$ to $R_9$ as defined for formula (Ia) to give an oligomer of the formula (Ia") with $R_1$ to $R_5$ and $R_7$ to $R_9$ as defined for formula (Ia) and L'=2 to 25, preferably 2 to 15, more preferably 2 to 9.

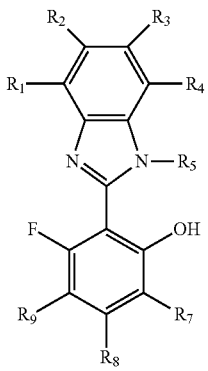

(Ia')

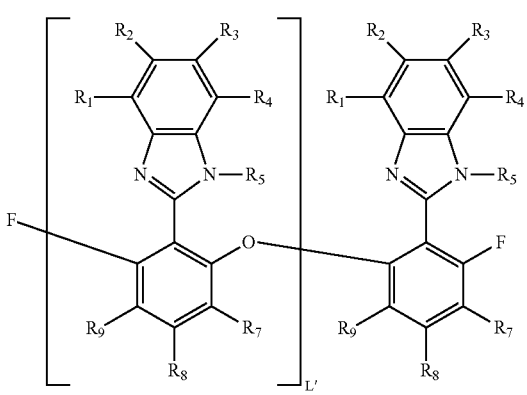

(Ia")

The process according to the invention preferably has a process step (4) in which a compound of the formula (Ia) or (Ia") as defined above is reacted with a diol, preferably hydroquinone.

The reaction in process step (4) is preferably effected as described hereinafter in a reaction vessel into which the compound of the formula (Ia) or (Ia"), $K_2CO_3$, hydroquinone are rinsed with DMAc. Preferably under an inert gas atmosphere, preferably a nitrogen atmosphere, the mixture is heated to boiling, preferably while stirring. At the top of the reaction vessel, any methanol and/or water formed is removed.

The process according to the invention preferably has a process step (5) in which the reaction product of diol, preferably hydroquinone, with a compound of the formula (Ia) or formula (Ia") as defined above is reacted with a compound of the formula (XIII)

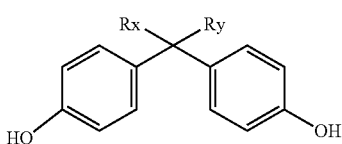

(XIII)

where Rx and Ry are the same or different and are alkyl or perfluoroalkyl, preferably a methyl, ethyl, propyl, isopropyl, n-butyl, tert-butyl or trifluoromethyl radical, more preferably —$CH_3$ or —$CF_3$, and a difluoro compound, preferably 4,4'-difluorobenzophenone or a compound of the formula (XIV)

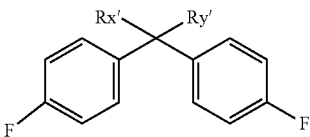

(XIV)

where Rx' and Ry' are the same or different and are alkyl or perfluoroalkyl, preferably a methyl, ethyl, propyl, isopropyl, n-butyl, tert-butyl or trifluoromethyl radical, more preferably —$CH_3$ oder —$CF_3$.

Preference is given to conducting process step (5) as follows: At room temperature, 4,4'-difluorobenzophenone (DFBP) and a compound of the formula (XIII), preferably bisphenol A, is added to the reaction mixture obtained in step (4), optionally with addition of a solvent, preferably DMAc, and optionally addition of $K_2CO_3$. This reaction mixture is heated to boiling and kept at boiling for from 10 to 30 hours, preferably from 12 to 25 hours, while water of reaction that forms during the reaction, especially on commencement of the reaction, is drawn off.

After cooling, the polymer can be precipitated from water. It may be advantageous to comminute the precipitated polymer, for example using an Ultraturrax, and then to wash (leach) it once or more than once with water and optionally subsequently with ethanol. Advantageously, the polymer, after the washing at elevated temperature and under reduced pressure, preferably at 125° C. to 160° C. and a slightly reduced pressure (reduced pressure of less than 500 mbar, preferably of about 200 mbar), is dried.

Preferably, the product obtained in process step (5) is reacted in a further process step (6) with an alkylating reagent, preferably methylating reagent. Preferably, process step (6) is conducted in such a way that the polymer obtained in process step (5) is dissolved in a solvent, e.g. N,N-dimethylacetamide, preferably at a temperature of 30 to 70° C., preferably 45 to 55° C., preferably while gently stirring. After the solution obtained has been cooled, it is brought to a temperature of 20 to 40° C., preferably 25 to 35° C., and iodomethane is added dropwise while stirring, for example via a syringe. After a period of preferably 0.25 to 5 hours, more preferably 1.5 to 2.5 hours, in which stirring is preferably continued, a vacuum pump is used to apply a reduced pressure of less than 500 mbar, preferably of about 200 mbar, in order to draw off excess iodomethane.

Preferred processes according to the invention are those that have one or more of the preferably or more preferably used process steps, preferably all process steps (1) to (6).

The above-described polymeric compounds according to the invention can be used, for example, as anion-conducting membrane for production of an anion-conducting membrane or for production of a component which is used in an electrochemical process, preferably selected from electrolysis, electrodialysis and fuel cell technology.

Correspondingly, it is a feature of membranes and electrolysers according to the invention that they include a compound, oligomer or polymer, preferably polymer, according to the invention.

For production of a membrane (according to the invention), especially an anion-conducting membrane, it is possible to directly use the solution obtained in process step (6). Preferably, the membrane is first produced in such a way that the required amount of polymer solution is taken up with a syringe or the like and applied preferably through a PTFE filter (for removal of any undissolved polymer particles) to a preheated glass plate, preferably preheated to 30° C. to 40° C. For the coating of the glass plate, preference is given to using a coating bar having a gap of preferably 350 μm, which is drawn automatically across the glass plate at a speed of 1 to 50 mm/s, preferably 2 to 5 mm/s. The wet layer applied is preferably predried under an inert gas, preferably nitrogen, for at least 10 hours, preferably from 12 to 10 hours. The predrying can be effected at room temperature or elevated temperature. The predrying is preferably effected at room temperature. The predrying is preferably followed by drying under reduced pressure, preferably at a pressure of less than 200 mbar$_{abs}$, preferably not more than 100 mbar$_{abs}$, and at a temperature above 25° C., preferably in the range from 40 to 80° C., preferably 55 to 65° C.

For production of the anion-conducting membrane, the membrane thus produced can be subjected to (aqueous) treatment, for example with 0.5 M KOH or KCl solutions. For this purpose, the membrane can be placed into the appropriate solution repeatedly, preferably 3 times for 1 hour each time at 60° C., and then stored in fresh solution at room temperature overnight. It may be advantageous when the membrane thus treated is then rinsed off with deionized water and placed repeatedly, preferably 3 times for 1 hour each time at 60° C., in fresh portions of deionized water and then stored at room temperature in a fresh portion of deionized water.

The examples adduced hereinafter describe the present invention by way of example, without any intention that the invention, the scope of application of which is apparent from the entirety of the description and the claims, be restricted to the embodiments specified in the examples.

EXAMPLES

Example 1: Synthesis of 2-(2',6'-difluorophenyl)benzimidazole (DFP-BI)

1600 g of polyphosphoric acid were transferred into a 3 l reaction vessel with a temperature-regulated oil bath, a mechanical stirrer system, an inlet for nitrogen and a long, ascending glass tube as cooler, and the oil bath was heated to 120° C. Subsequently, 632 g of 2,6-difluorobenzoic acid (DFBA) were stirred in gradually. 432 g of ortho-phenylenediamine were stirred into this mixture over the course of one hour. The temperature of the oil bath was kept at 125° C. for one day, at 135° C. for one day, at 145° C. for 3 days and at 150° C. for 1 day. The DFBA which had sublimed in long needles on the colder surfaces of the reactor was repeatedly rinsed back into the reaction mixture by adding a few millilitres of tetrahydrofuran (THF), which evaporated and condensed at the colder sites. The reaction mixture was cooled down and diluted gradually to a total volume of 3 l with water at about 80° C. This precipitated the dihydrogenphosphate of the DFP-BI out of the solution. This precipitate was filtered off with suction, and twice slurried with two litres of water each time and filtered off with suction. The still-wet filtercake was slurried in a solution of 250 g of NaOH in 1.5 l of water, which released the DFP-BI from its dihydrogenphosphate. After stirring for one hour, the mixture was filtered with suction. The filtercake was slurried in 2 l of water and brought to a pH of 9 with ammonium hydroxide solution. This purification was repeated with pure water. The filtercake that had been filtered off with suction was dried at 120° C. at 30 mbar overnight. Crude yield: 810 g of pale pink product, which is 88% of the theoretical yield.

This product can be purified by recrystallizing from THF. The product purified in this way was examined by means of $^1$H and $^{13}$C NMR and identified unambiguously as 2-(2',6'-difluorophenyl)benzimidazole.

Example 2: Methylation of DFP-BI to MeDFP-BI

The apparatus consisted of a 1 l four-neck flask with mechanical stirrer, nitrogen blanketing, a temperature-regulated aluminium heating block and a column having random packing of length 35 cm and diameter 2 cm, filled with Raschig rings. Placed atop the column was a cooler with adjustable reflux ratio and condensate withdrawal.

At room temperature, 34.50 g of DFP-BI from Example 1 (recrystallized from THF), 26.1 g of dimethyl carbonate dissolved in 75 g of dimethylacetamide (DMAc), 10.35 g of ground K$_2$CO$_3$ were added and the mixture was reacted at heating block temperature 95° C. for 1 hour, at 100° C. for 15 hours and at 125° C. for another 1 hour. Subsequently, the block temperature was adjusted to 100° C. under closed-loop control, 9.0 ml of water were added and the mixture was stirred for another 1 hour in order to break down excess dimethyl carbonate.

Example 3: Oligomerization of MeDFP-BI

The mixture from Example 2 was cooled down to room temperature and 13.8 g of K$_2$CO$_3$ (ground and dried at 400° C.) and 17.60 g of hydroquinone were flushed into the apparatus with 50 g of DMAc, the apparatus was flooded with nitrogen for 20 minutes and then the mixture was heated to boiling while stirring, by adjusting the heating block temperature to 225° C. under closed-loop control. At the top of the column, first methanol and then water were drawn off in that order. Water that had formed in the reaction was removed continuously via the column. After 18 hours, a slurry of 10.3 g of K$_2$CO$_3$ in 20 g of DMAc was added and the mixture was reacted at boiling for a further 5 hours.

Example 4: Polymerization

The mixture from Example 3 was cooled down to room temperature and 32.70 g of 4,4'-difluorobenzophenone (DFBP), 31.92 g of bisphenol A (BPA) and 10.3 g of K$_2$CO$_3$ and 130 g of DMAc were added and the mixture was kept at boiling for a further 20 hours, while drawing off the water of reaction at the top of the column specifically at the start. Then another 3.45 g of K$_2$CO$_3$ were added to the already viscous solution and the mixture was kept at boiling temperature for a further 3 hours.

Example 5: Workup of the Polymer

After the reaction mixture from Example 4 had been cooled, the reaction mixture was precipitated in 2 l of water, and the precipitated polymer was comminuted with the aid of an Ultraturrax and leached twice with water at 80° C. Finally, the polymer was also leached with 500 ml of ethanol at 60° C. The polymer was filtered off with suction and then dried at 150° C. under reduced pressure. Yield: 106 g of almost white product.

Example 6

Synthesis of 1-methyl-2-(2',6'-difluorophenyl)benzimidazole (MeDFP-BI)

1500 g of dimethylformamide (DMF), 100 g of K$_2$CO$_3$ and 4.5 mol of dimethyl carbonate (DMC) were introduced into a 3 l reaction vessel with an oil bath under closed-loop control by the internal temperature, a mechanical stirrer system, an inlet for nitrogen and a reflux condenser.

690 g of DFP-BI (crude product from Example 1) was divided into two batches of 400 g and 290 g. The first batch was introduced into the reactor. The reaction solution was first adjusted to a temperature of 95° C. for half an hour and to 100° C. for a further 5 hours under closed-loop control. After it had been cooled down, the second batch was added, and the mixture was adjusted to a temperature of 95° C. for half an hour, to 100° C. for a further 5 hours and to 125° C. for three hours under closed-loop control.

After it had been cooled down to room temperature, the reaction solution was stirred in 5 l of water. In the course of this, a solid material precipitated out. This was filtered off, washed with water and dried at 90° C. under reduced pressure overnight.

Crude yield: 660 g

Example 7

Synthesis of 1-methyl-2-(2'-hydroxy-6'-fluorophenyl)benzimidazole (MeHyFP-BI)

The apparatus consisted of a 3 l reaction vessel with mechanical stirrer, nitrogen blanketing, a temperature-regulated oil bath and a column having random packing of length 35 cm and diameter 2 cm, filled with Raschig rings. Placed atop the column was a cooler with adjustable reflux ratio and condensate withdrawal.

The reactor was charged at room temperature with 488 g of MeDFP-BI from Example 6, 300 g of KOH in the form of flakes, 100 g of hexamethyldisiloxane (HMDS) and 800 g of sulfolane. The oil bath was adjusted to a temperature of 105° C. under closed-loop control. Shortly thereafter, the solution began to boil vigorously owing to the exothermic reaction. Shortly thereafter, there was a decrease in the amount of HMDS evaporating, and for that reason the temperature of the oil bath was increased gradually, so that the solution continued to boil.

After 7 h, some of the HMDS was drawn off at the top of the column and then cooled down. When the temperature went below about 70° C., the reaction solution was diluted with 1.5 l of water. The solution was slightly cloudy and was filtered at room temperature through a G3 frit. The clear filtrate was neutralized with acetic acid. In the course of this, the MeHyFP-BI precipitated out, and was filtered off with suction and washed with water. The filtercake was slurried in 2.5 l of water and acidified down to pH about 0 with concentrated hydrochloric acid. On heating to 80° C., the MeHyFP-BI precipitated out as the hydrochloride and the solution was hot-filtered. The hydrochloride separated out of the cooling filtrate in the form of white crystals. It was filtered off with suction. The filtrate was neutralized with ammonia solution, and MeHyFP-BI precipitated out (fraction 2).

The hydrochloride that had been filtered off with suction was slurried in water, and MeHyFP-BI was likewise released with ammonia solution and filtered off (fraction 1). The two fractions were dried at 100° C. under reduced pressure overnight.

Fraction 1: 431 g; very clean by HPLC
Fraction 2: 40.5 g; pale pink, probably impure Example 8: Trimerization of MeDFP-BI and MeHyFP-BI from Example 6 to Give the Macromer 0.0500 mol (12.20 g) of MeDFP-BI, 0.1000 mol (24.20 g) of MeHyFP-BI, 0.1014 mol (14.0 g) of $K_2CO_3$ were transferred into a 500 ml three-neck flask with mechanical stirrer, a column having random packing (L=35 cm, D=2 cm) with a column head, a temperature-regulated aluminium heating block and a nitrogen purge with 70 g of DMAc, and purged with nitrogen for 30 minutes. Subsequently, the heating block was heated to 225° C. and the solution began to boil. Water of reaction formed was drawn off continuously at the column head. After 20 hours, the heating block was cooled down to room temperature.

Example 9: Oligomerization of Macromer from Example 7 with Hydroquinone to Give the Oligomer 6.60 g of hydroquinone, and also 8.40 g of $K_2CO_3$ and 25 g of DMAc, were added under nitrogen to the cooled reaction mixture from Example 8 and the heating block was heated again to 225° C. Water of reaction formed was drawn off continuously at the column head. After 16 hours, the reaction solution was cooled down to room temperature.

Example 10: Polymerization of the Oligomer from Example 9 to Give the Block Copolymer 10.90 g of 4,4'-difluorobenzophenone and the first 12.00 g of a total amount of 13.44 g of 2,2'-(4'-hydroxyphenyl) hexafluoropropane (BPA-6F), and also 8.40 g of $K_2CO_3$ and 70 g of DMAc, were added under nitrogen to the cooled reaction mixture from Example 9. The heating block was heated again to 225° C. Water of reaction formed was drawn off continuously at the column head. After a reaction time of 3 hours, 1.00 g of BPA-6F, and also 1.00 g of $K_2CO_3$ and 10 g of DMAc, were added and the temperature of the heating block was adjusted to 200° C. under closed-loop control. After a further 3 hours, the remaining 0.44 g of BPA-6F was added, and the heating block was adjusted to 190° C. under closed-loop control and kept at this temperature for another 3 further hours. Thereafter, the mixture was cooled down to room temperature and the polymer was worked up analogously to Example 5.

Example 11: Quaternization of the Polymer with Iodomethane

For quaternization of the polymer, 15 g of the product from Example 10 were dissolved in 45 g of N,N-dimethylacetamide in the flask at 50° C. with gentle stirring and the mixture was stirred for about one hour until dissolution of the polymer was complete. After the solution had been cooled down to 30° C., 6.6 g of iodomethane were added by gradual dropwise addition via a syringe and the solution was stirred for a further 2 hours. The unconsumed iodomethane was then drawn off with a vacuum pump at 200 mbar and the gas phase was passed through two gas wash bottles filled with 30% by mass aqueous KOH solution and arranged in series to break down the iodomethane.

Example 12: Quaternization of the Polymer with Dimethyl Sulfate

The polymer was quaternized by dissolving 3.0 g of the product from Example 10 in 7 g of DMF in the flask at 50° C. while stirring. After the solution had been cooled down to 25° C., 1.1 g of dimethyl sulfate were added dropwise and the mixture was stirred. The exothermic reaction began slowly at first, the reaction mixture warmed up to above 45° C. and the reaction was completed after a few minutes at this temperature.

Example 13: Production of the Membrane

The solution of the quaternized polymer described in Example 11 was used directly for production of the membrane. The required amount of polymer solution was taken up with a syringe and applied directly through a PTFE filter (for removal of any undissolved polymer particles) to a glass plate preheated to 30° C. For the coating of the glass plate, a coating bar having a gap of preferably 350 μm was used, which was drawn automatically across the glass plate at a speed of 5 mm/s. The wet layer applied was predried at room temperature under nitrogen for 16 hours and then dried at 60° C. under reduced pressure for 6 hours.

Example 14: Ion Exchange of the Membrane

The membrane produced in Example 13 was ion-exchanged, meaning that the iodide ions present as a result of the quaternization of the polymer were exchanged for chloride or hydroxide ions. For this purpose, the membrane samples that had been cut to size were placed into aqueous 0.5 M KOH solution 3 times at 60° C. for 1 hour each time and then stored in fresh 0.5 M KOH solution at room temperature overnight. After the ion exchange, the membrane samples were rinsed off with deionized water and placed 3 times at 60° C. for 1 hour each time in fresh portions of deionized water. Subsequently, the membrane samples were stored in a fresh portion of deionized water at room temperature overnight.

Example 15: Determination of the Ionic Conductivity of the Membrane

The in-plane, i.e. two-dimensional, ionic conductivity of the ion-exchanged membrane samples was measured by means of impedance spectroscopy (EIS) in a standard 4-electrode arrangement. The membrane sample was secured in a commercial BT-112 cell (Bekk Tech LLC) such that the two outer Pt wires were positioned beneath the sample and the two middle wires above the sample. The BT-112 cell was positioned between 2 PTFE sheets and filled with DI water. The temperature of the DI water was controlled by means of a water bath and DE water was pumped permanently through the cell. The calculation of the resistance ($R_{membrane}$) was conducted by the fitting of the EIS spectrum by means of a widely used R(RC) Randles equivalent circuit. The ionic conductivity (σ) of the membrane sample is found from equation (1):

$$\sigma = L/(R_{membrane} * A) \quad (1)$$

with L the distance between Pt wires (5 mm) and A the area of the membrane sample between the two outer Pt wires.

Example 16: Determination of the Water Absorption of the Membrane

The ion-exchanged membrane samples (3 samples for each membrane tested) were dried in a vacuum oven at 40° C. and 25 mbar for 24 hours, then cooled down to room temperature in a desiccator and weighed. For the measurement of water absorption, the membrane samples were stored in deionized water equilibrated to 25° C. for 24 hours. Subsequently, the weight of each sample was redetermined. For this purpose, water still adhering was removed from the membrane with the aid of a filter paper. Each measurement was repeated 3 times and an average±standard deviation were calculated. The water absorption (WA) is calculated from equation (2):

$$WA = (m_{wet} - m_{dry})/m_{dry} * 100\% \quad (2)$$

with $m_{wet}$ the mass of the sample after swelling and $m_{dry}$ the dry mass of the sample.

Example 17: Determination of the Swelling Characteristics of the Membrane

The ion-exchanged membrane samples (3 samples for each membrane tested) were dried in a vacuum oven at 40° C. and 25 mbar for 24 hours, then cooled down to room temperature in a desiccator, and such parameters as the sample length, sample width and sample thickness were determined. For the determination of the swelling characteristics, the membrane samples were stored in deionized water equilibrated to 25° C. for 24 hours. Subsequently, the sample length, sample rate and sample thickness were redetermined. For this purpose, water still adhering was removed from the membrane with the aid of a filter paper. Each measurement was repeated 3 times and an average±standard deviation were calculated. The swelling characteristics (referred to as dimensional stability, DS) in terms of length, width and thickness are calculated from equation (3):

$$DS = (x_{wet} - x_{dry})/x_{dry} * 100\% \quad (3)$$

with $x_{wet}$ the length, width or thickness of the sample after swelling and $x_{dry}$ the dry length, dry wet or dry thickness of the sample.

Example 18: Determination of the Mechanical Durability of the Membrane

The ion-exchanged membrane samples (3 samples for each membrane tested) were stored in deionized water for 24 h. Before the sample was installed into the test system (DMA 8000 with water bath), the width and thickness of each membrane sample were determined repeatedly. The procedure for the measurement is as follows: membrane sample is installed between two statically prestressed vertical clamps opposite one another. In order to transmit a static prestress to the sample, during the installation, the distance between the clamps (also referred to as free path length l) is reduced by about 1 mm. The sample is fixed between the two clamps and then the original free path length is restored, which stretches the sample. The entire test setup is immersed in a heatable water bath with deionized water, such that the sample is completely surrounded by water. The test procedure comprises the analysis of the sample within a temperature range between room temperature (about 23° C.) and 80° C. at an applied heating rate of 2 K/min. Within this temperature interval, the sample is placed under continuous stress in a sinusoidal manner with an elongation ε of 0.1% at a frequency of 1 Hz. The elongation in % is calculated from equation (4):

$$\varepsilon = \Delta l/l \quad (4)$$

with Δl the sample elongation in mm and l the free path length. Given a free path length of l=10 mm, when ε=0.1%, an elongation of 0.01 mm is found. A force sensor detects the tension required for the defined elongation. The results of the test are reported in Table 1.

TABLE 1

| | Water absorption [%] | Dimensional stability[1] [%] | Ionic conductivity[2] [mS/cm] | Ionic conductivity[3] [mS/cm] | Mechanical durability[4] [GPa] |
|---|---|---|---|---|---|
| Membrane 1 | 8.1 ± 1.1 | 4.6 ± 1.1 | 6.4 ± 0.4 | — | 1.429 ± 0.101 |
| Membrane 2 | 3.2 ± 0.9 | 4.2 ± 0.1 | 51.3 ± 1.2 | — | 0.853 ± 0.037 |
| FAA-3 | 28.4 ± 8.8 | 13.1 ± 2.7 | 30.9 ± 3.4 | — | 0.086 ± 0.01 |
| Nafion N-115 | 14.0 ± 0.7 | 5.1 ± 0.5 | — | 110.7 ± 4.8 | 0.085 ± 0.01 |

Elucidations

Membrane 1 was produced from the polymer described in Example 5 and then quaternized.

Membrane 2 was produced from the polymer described in Example 10 and then quaternized.

FAA-3 is a commercially available anion-conducting membrane from FUMATECH BWT GmbH.

Nafion N-115 is a commercially available cation-conducting membrane from The Chemours Company (USA).

The invention claimed is:

1. A compound containing a unit of the formula (Ia) or (Ib)

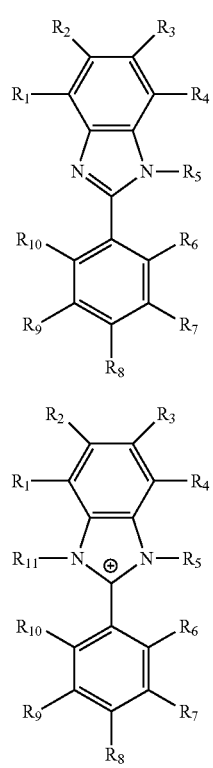

wherein $R_1$, $R_2$, $R_3$ and $R_4$ are the same or different and are —H or any desired group, $R_5$ and $R_{11}$ are the same or different and are an alkyl or perfluoroalkyl radical, $R_6$ and $R_{10}$ are the same or different and are an oligomer or polymer radical, wherein at least one of the $R_6$ or $R_{10}$ radicals is an oligomer or polymer radical attached via an oxygen atom to the ring carbon atom, and $R_7$, $R_8$ and $R_9$ are the same or different and are —H or any desired group.

2. The compound according to claim 1, wherein the compound is an oligomer or polymer having at least 2 units of the formula (Ia) or (Ib).

3. The compound according to claim 1, wherein $R_6$ and $R_{10}$ represent a polymer radical.

4. The compound according to claim 1, wherein the compound is a polymer compound wherein the polymer radicals $R_6$ and $R_{10}$ have one or more units of the formula (IIa) and/or (IIb) and/or (IIIa) and/or (IIIb)

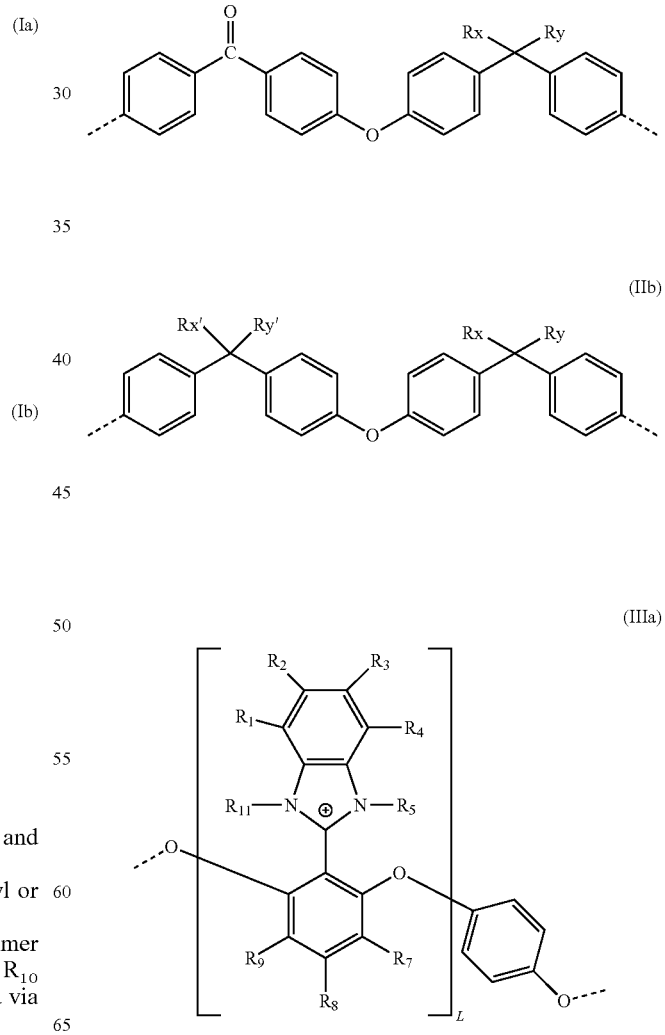

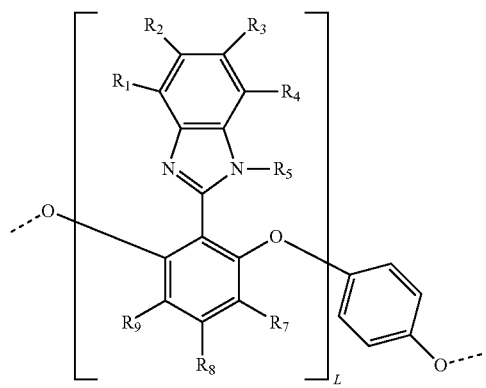
(IIIb)
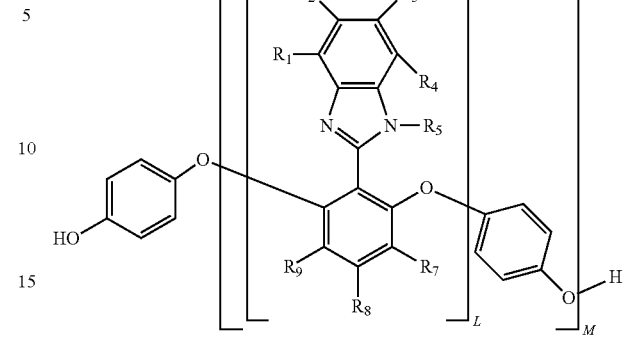
(IVc)
wherein L=1 to 25 and where Rx and Ry and Rx' and Ry' are the same or different and are an alkyl, phenyl or perfluoroalkyl radical.
5. The compound according to claim 1, wherein the compound is of the formula (IVa), (IVb), (IVc), (IVd), (IVe) or (IVf)
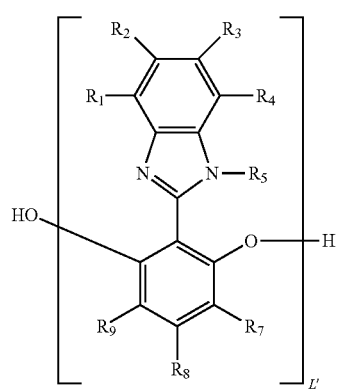
(IVa)
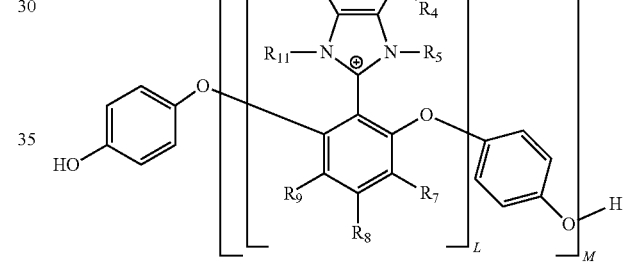
(IVd)
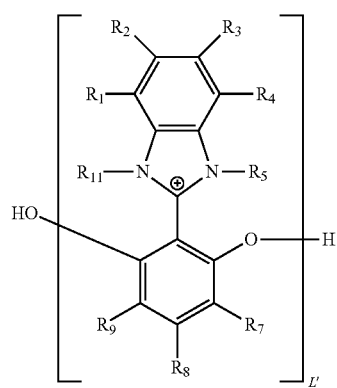
(IVb)
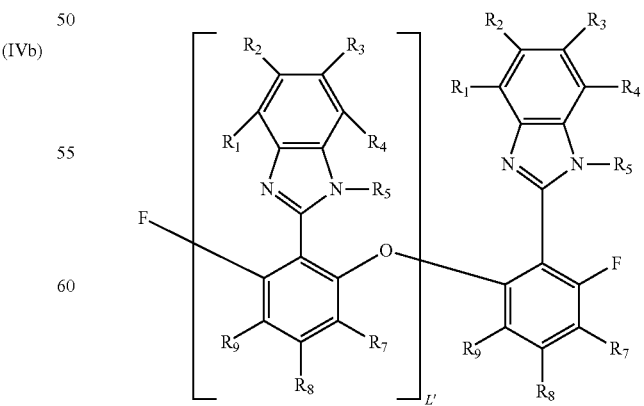
(IVe)

(IVf)
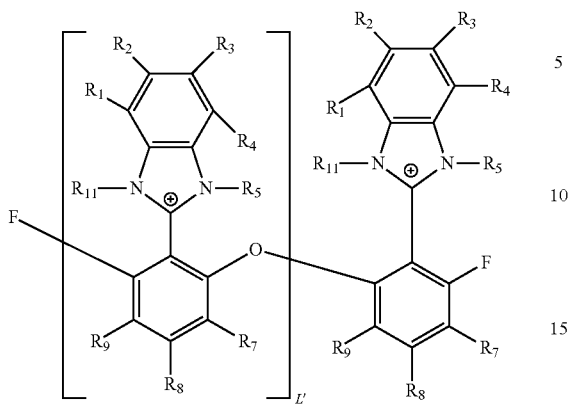
wherein L=1 to 25 and L'=2 to 25 and M=1 to 500.
6. The compound according to claim 1, wherein the compound is of the formula (Va) or (Vb)
(Va)
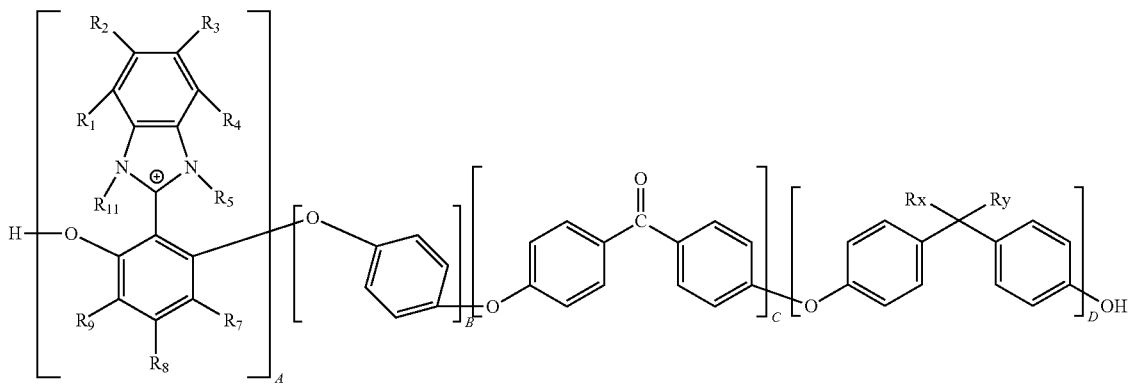
(Vb)
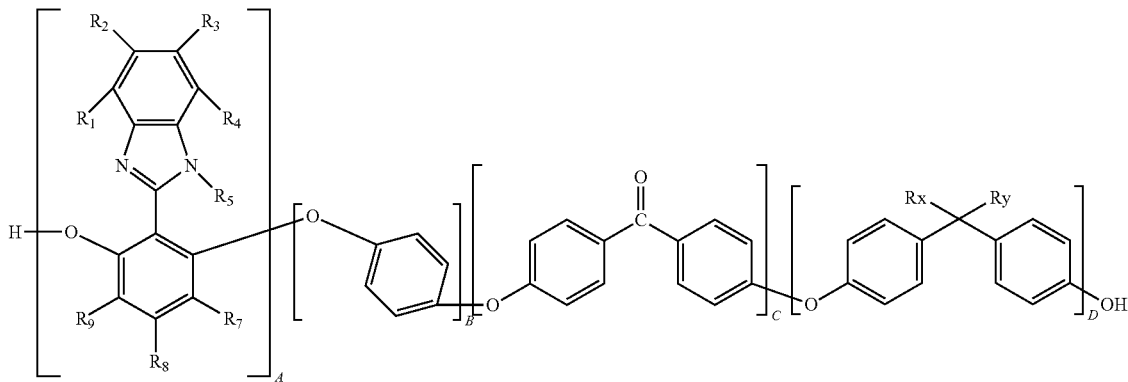
wherein Rx and Ry are the same or different and are —CH₃ or —CF₃ and A=5 to 500, B=5 to 500, C=1 to 500 and D=0 to 1000, where the units indicated by the indices A, B, C and D may occur in blockwise or random distribution in the compound.

7. The compound according to claim 1 wherein the compound is of the formula (VIa) to (VId)
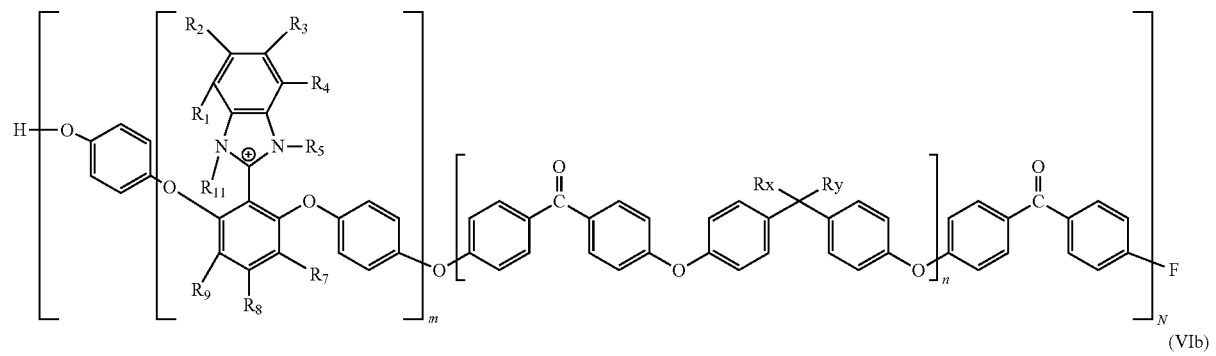
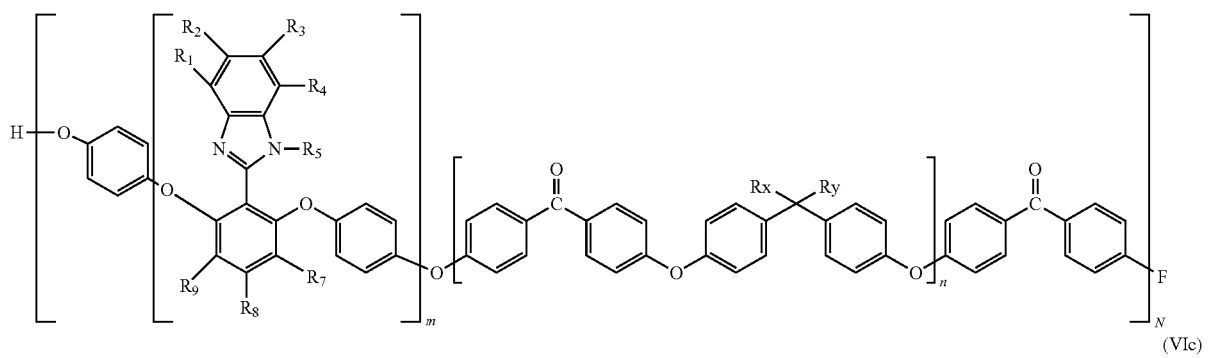
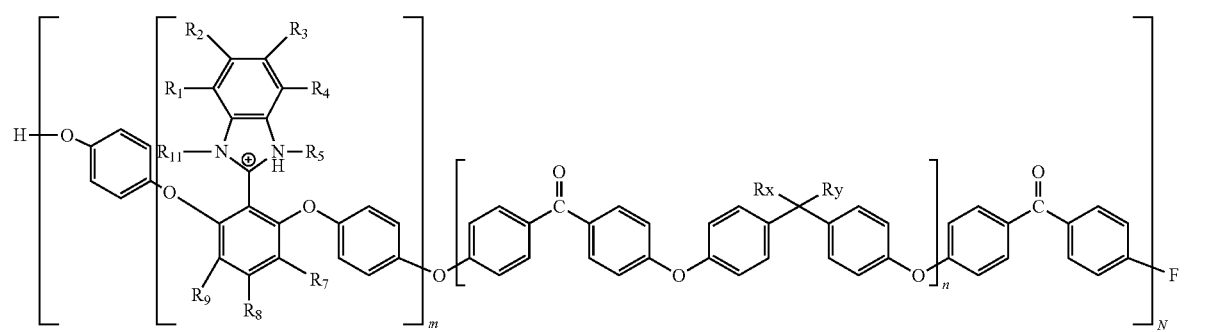
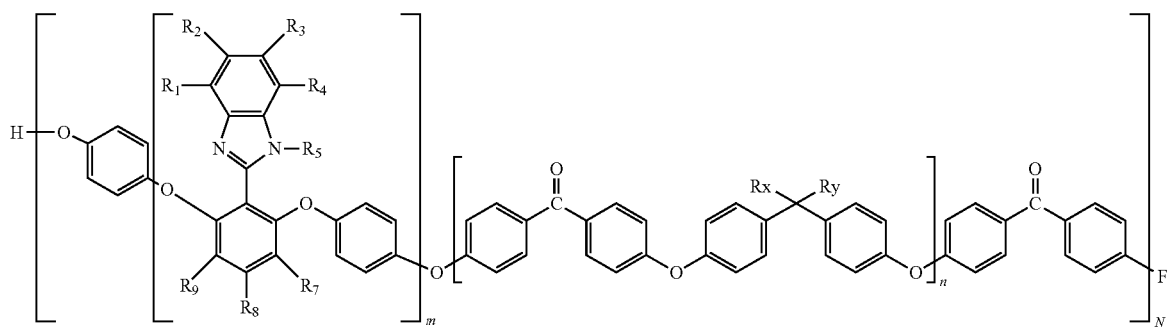
wherein L=1 to 25 and where Rx and Ry are the same or different and are —CH$_3$ or —CF$_3$ and m=1 to 500, n=1 to 500 and N=1 to 500, where the units indicated by the indices m, n and N may occur in blockwise or random distribution in the compound.

8. A process for preparing a compound of claim 1, wherein the process comprises a step in which a compound of the formula (X)

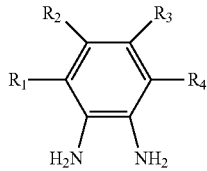
(X)

wherein $R_1$, $R_2$, $R_3$ and $R_4$ are the same or different and are —H or any desired group, is reacted with a compound of the formula (XI)

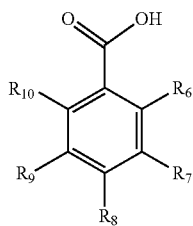
(XI)

wherein $R_7$, $R_8$ and $R_9$ are the same or different and are —H or any desired group, and $R_6$ and $R_{10}$=—F, to give a compound (XII)

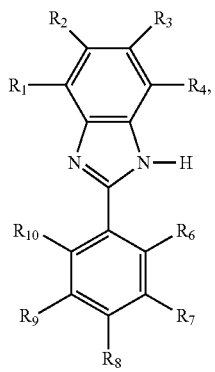
(XII)

wherein $R_1$, $R_2$, $R_3$, $R_4$, $R_7$, $R_8$ and $R_9$ are the same or different and are —H or any desired group and $R_6$ and $R_{10}$=—F, and the compound of the formula (XII) is reacted with a methylating reagent or trifluoromethylating reagent to obtain a compound as follows

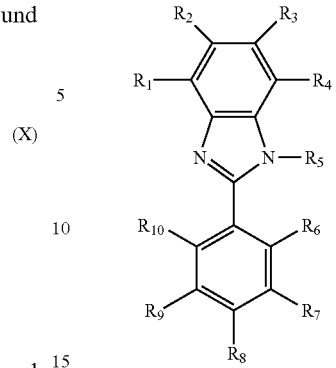

wherein $R_1$, $R_2$, $R_3$, $R_4$, $R_7$, $R_8$ and $R_9$ are the same or different and are —H or any desired group,
$R_5$=alkyl or perfluoroalkyl radical and R6 and R10=—F, and
wherein the process further includes a subsequent process step to form the compound of claim 1.

9. The process according to claim 8, having a process step in which the compound of claim 1 is reacted with a compound of the formula (Ia') to give an oligomer of the formula (Ia'').

10. The process according to claim 9, having a process step in which the reaction product of the compound of claim 1 or formula (Ia'') is reacted with a compound of the formula (XIII)

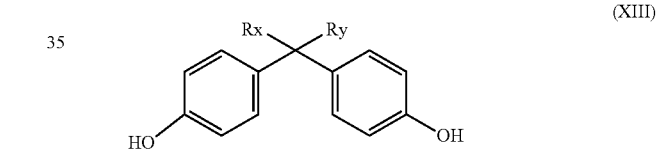
(XIII)

where Rx and Ry are the same or different and are an alkyl or perfluoroalkyl radical, and a difluoro compound or a compound of the formula (XIV)

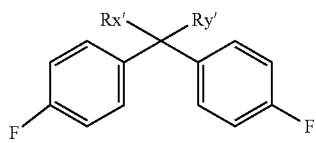
(XIV)

where Rx' and Ry' are the same or different and are an alkyl or perfluoroalkyl radical.

11. The process according to claim 10, having a process step in which the compound of claim 1 is reacted with a compound of the formula (Ia') to give an oligomer of the formula (Ia'') and reacting the oligomer of the formula (Ia'') with an alkylating reagent.

12. An anion-conducting membrane comprising the compound according to claim 1.

13. An electrolyzer comprising the compound according to claim 1.

14. The compound according to claim 1, wherein
$R_1$, $R_2$, $R_3$ and $R_4$ are —H, and
$R_7$, $R_8$ and $R_9$ are —H.

15. The compound according to claim 4, wherein
L=from 1 to 9.
16. The compound according to claim 5, wherein
L=from 1 to 9, and
L'=3 to 9.
17. The compound according to claim 7, wherein
L=from 1 to 9, and
n=5 to 50.

\* \* \* \* \*